United States Patent [19]

Kelman

[11] 4,253,200
[45] Mar. 3, 1981

[54] INTRAOCULAR LENSES

[76] Inventor: Charles D. Kelman, 73 Bacon Rd., Old Westbury, N.Y. 11568

[21] Appl. No.: 95,056

[22] Filed: Nov. 16, 1979

[51] Int. Cl.³ .......................... A61F 1/16; A61F 1/24
[52] U.S. Cl. ............................................................. 3/13
[58] Field of Search ............................................. 3/13, 1

[56] References Cited

U.S. PATENT DOCUMENTS

| | | | |
|---|---|---|---|
| 4,092,743 | 6/1978 | Kelman | 3/13 |
| 4,159,546 | 7/1979 | Shearing | 3/13 |

FOREIGN PATENT DOCUMENTS 2717706  10/1978  Fed. Rep. of Germany ................. 3/13

OTHER PUBLICATIONS

"The Lens", (one p.), published 1977, Shearing Posterior Chamber Lens, (Model 101).

*Primary Examiner*—Ronald L. Frinks
*Attorney, Agent, or Firm*—Philip Rodman

[57] ABSTRACT

An intraocular lens with a medial light-focusing lens body includes oppositely disposed position fixation means with respective seating portions that are resiliently retained in the eye without sutures. One of the position fixation means is adapted to be seated forwardly of the other position fixation means with respect to the optical axis of the eye. After the intraocular lens has been inserted in the eye the seating portion of the forwardly disposed position fixation means has a greater radial extent from the optical axis of the eye than the seating portion of the rearwardly disposed position fixation member.

27 Claims, 6 Drawing Figures

INTRAOCULAR LENSES

This invention relates to intraocular lenses for the human eye and more particularly to an intraocular lens having one support member that is seated forwardly of another support member in the eye.

The placement or insertion of an intraocular lens in the eye is a well known and widely used technique for restoring vision after a cataract removal operation. The natural structure of the eye furnishes a variety of locations for fixing the position of an intraocular lens in the eye. For example, an intraocular lens can be supported anteriorly of the iris between the scleral spur and the iris as disclosed in my patent application Ser. No. 911,452 filed June 1, 1978, now U.S. Pat. No. 4,174,543. Alternatively, an intraocular lens can be supported posteriorly of the iris between the anterior and posterior capsule walls as disclosed in my U.S. Pat. No. 4,092,743.

It is often desirable to support the intraocular lens posteriorly of the iris between the anterior and posterior capsule walls, preferably without suturing. However, such positioning cannot always be achieved because the extent of anterior wall structure at the upper portion of the eye that remains after cataract surgery is usually insufficient to accommodate and hold a position fixation member of the intraocular lens without suturing. Therefore since suturing might be necessary to secure the position fixation member to the upper anterior capsule wall of the eye other locations in the eye which do not require sutures are likely to be considered.

It has been found that a posterior chamber, two-loop intraocular lens such as Model PC-10 made by Heyer-Schulte Medical Optics Center of Irvine, California, can be positioned without sutures in the ciliary sulcus of the eye between the iris and the anterior capsule wall. The posterior chamber, two-loop intraocular lens comprises a medial light-focusing lens body with a pair of oppositely disposed, dimensionally equivalent position fixation members in the general shape of a J. The J-shaped position fixation members are usually formed of a plastic such as polypropylene having sufficient spring-like quality to provide a resilient locking of the lens body in the ciliary sulcus of the eye. Although resilient contact of the position fixation members in the ciliary sulcus provides stable positioning of the lens body in the eye without sutures, the total force exerted by the position fixation members on the ciliary sulcus may in some instances reach an undesirable level.

The known posterior chamber two-loop intraocular lens, after insertion in an eye, may require further adjustments of the position fixation members to achieve optimum positioning of the lens body. Often an adjustment need only be made to one of the position fixation members. However, because the ciliary sulcus is not as accessible as other regions of the eye it is difficult to ascertain which of the position fixation members require further adjustment. Therefore, it is usually necessary to check, adjust, and readjust each of the position fixation members as assurance that optimum positioning of the posterior chamber, two-loop intraocular lens has been accomplished.

It is thus desirable to provide an intraocular lens which can be positioned in the eye posteriorly of the iris without suturing, with relatively easy adjustment, and which will minimize the overall force on the ciliary sulcus.

Among the several objects of the present invention may be noted the provision of an intraocular lens having two oppositely disposed position fixation members, one of which is adapted to be resiliently retained in the ciliary sulcus and the other of which is adapted to be resiliently retained between the anterior and posterior capsule walls, and an intraocular lens which imposes substantially less force on the ciliary sulcus than the posterior chamber, two-loop intraocular lens.

Other objects and features will be in part apparent and in part pointed out hereinafter.

The present invention relates to a novel intraocular lens having a lens body with two oppositely disposed position fixation members, one of the position fixation members having means for permitting it to be seated in the eye forwardly of the other position fixation member with respect to the optical axis of the eye. To facilitate description of the structure disclosed herein it will be presumed that the eye has an optical axis passing through the center of the pupil. It will also be presumed that when the intraocular lens is inserted in an optimum position in the eye the optical axis of the lens body substantially aligns with the optical axis of the eye.

In an average human eye the distance from the optical axis of the eye to the inner peripheral surface of the ciliary sulcus is approximately one to two millimeters greater than the distance from the optical axis to the inner peripheral surface of a circumferential cul-de-sac portion of the eye between the anterior and posterior capsule walls.

In one embodiment of the invention the seating portions of each position fixation member are substantially equidistant from the optical axis of the lens body but the deflective stiffness of the position fixation members is different. Thus when equal forces are presented against the seating portions of each position fixation member the softer member will deflect a greater amount than the stiffer member. The stiffer member can thus be seated in the ciliary sulcus for example, and the softer member can be seated rearwardly of the stiffer member in the circumferential cul-de-sac portion of the eye formed between the anterior and posterior capsule walls. The softer position fixation member is thus structured to deflect approximately one to two millimeters more than the stiffer position fixation member under equal force conditions. The seating portions of the position fixation members can have a generally coplanar arrangement with the lens body. Therefore, when one position fixation member is seated forwardly of the other, the lens body is tilted slightly with respect to the pupil of the eye. Such inclination is acceptable since it is approximately 10° from the vertical.

In another embodiment of the invention the seating portion of one position fixation member is approximately one to two millimeters less distant from the optical axis of the lens body than the seating portion of the other position fixation member and the deflective stiffness of the position fixation members is substantially equivalent. As with the previous embodiment the seating portions of the position fixation members can have a generally coplanar arrangement which leads to a slight tilt of the lens body with respect to the pupil of the eye.

In another embodiment of the invention the seating portion of one position fixation member is also approximately one to two millimeters less distant from the optical axis of the lens body than the seating portion of the other position fixation member. The deflective stiffness of the position fixation members is substantially equivalent but one of the position fixation members is inclined with respect to the lens body so that its seating portion is offset forwardly from the seating portion of the other position fixation member approximately seven to twelve degrees. The offset between the seating portions enables the lens body to be substantially uninclined with respect to the pupil of the eye after insertion of the intraocular lens in the eye.

In a further embodiment of the invention the position fixation members have substantially equivalent deflective stiffness and the respective seating portions have a one to two millimeter difference in extent from the optical axis of the lens body. However, one of the position fixation members is formed with a step to provide an offset of its seating portion from the seating portion of the other position fixation member. The offset thus enables the lens body of the inserted intraocular lens to be substantially free of inclination with respect to the pupil of the eye.

In each of the embodiments of the intraocular insert the position fixation members are preferably integrally joined to the lens body. The lens body and the integrally joined position fixation members are inserted in the eye through a corneo-scleral incision for example, and the stiffer position fixation member or the one having the more remotely disposed seating portion with respect to the optical axis of the lens body is seated in the ciliary sulcus of the eye whereas the seating portion of the other position fixation member is seated in the circumferential cul-de-sac portion of the eye between the anterior and posterior capsule walls. The resilient spring-like characteristics of the position fixation members enables the intraocular lens to be maintained in position without suturing due to the resilient contact of one position fixation member against the ciliary sulcus, and the resilient contact of the other position fixation member against the circumferential cul-de-sac portion between the anterior and posterior capsule wall surfaces.

Since only one of the position fixation members is disposed in the ciliary succus region of the eye there is less total force on this region after the intraocular lens has been inserted than that provided by the known posterior chamber, two-loop intraocular lens. Placement of one of the position fixation members in the circumferential cul-de-sac portion of the eye between the anterior and posterior capsule walls also facilitates positioning of the other position fixation member in the ciliary succus region.

The invention accordingly comprises the constructions hereinafter described, the scope of the invention being indicated in the following claims.

In the accompanying drawing in which various embodiments of the invention are illustrated, FIG. 1 is a simplified plan view of an intraocular insert incorporating one embodiment of the present invention;

Figure 1:
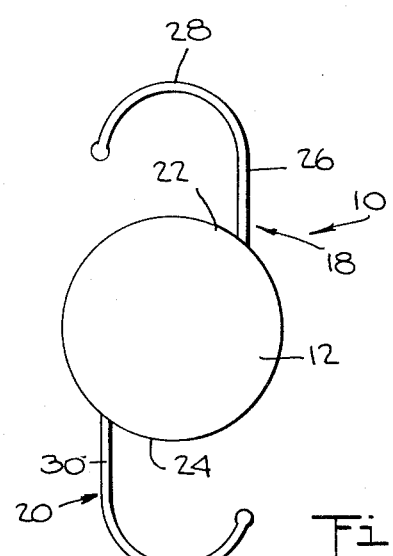

Referring now to the drawing, an intraocular insert incorporating one embodiment of the invention is generally indicated by reference number 10 in FIG. 1.

The intraocular insert includes a medial light-focusing lens body 12 having a convex or flat anterior surface 14 and a generally flat or convex posterior surface 16. A pair of position fixation members 18 and 20 are integrally joined to opposite peripheral sections 22 and 24 of the lens body 12.

The position fixation members 18 and 20 are preferably of J-shaped configuration. The position fixation member 18 has a leg portion 26 extending from the peripheral section 22 and terminates in a curved seating portion 28. The position fixation member 20 has a leg portion 30 extending from the peripheral section 24 and terminates in a curved seating portion 32.

The lens body 12 and the position fixation members 18 and 20 are formed of any suitable material which is compatible with the environment at the interior of the eyeball, such as a non-toxic plastic, for example polypropylene.

Figure 2:
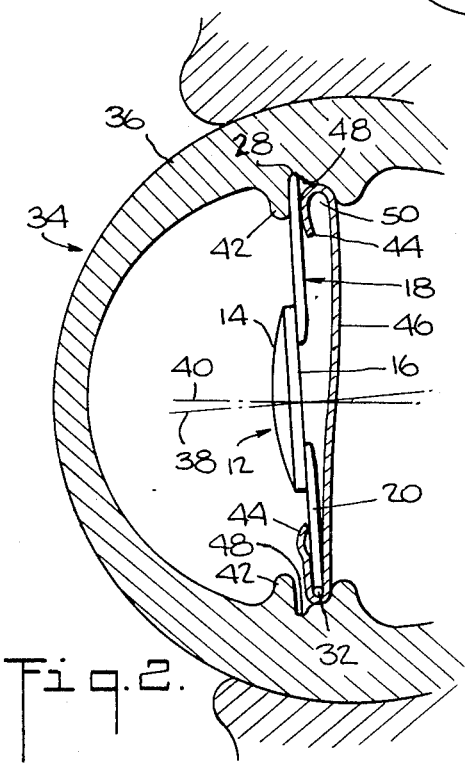
FIG. 2 is a simplified schematic sectional view of an eyeball with the intraocular insert seated therein.

Referring to FIG. 2, the intraocular insert 10 is inserted in an eyeball 34 using suitable known medical procedures, which include, for example, a corneo-scleral incision 36. Insertion of the intraocular insert 10 is preferably accomplished by orienting the lens body 12 so that one and only one of the position fixation members 18 and 20 enters the incision 36 before insertion of the other position fixation member.

For example, although the intermediate steps of insertion of the intraocular insert 10 are not shown, the position fixation member 20 first enters the incision 36 followed by entry of the lens body 12 and thereafter entry of the position fixation member 18.

Figure 4:
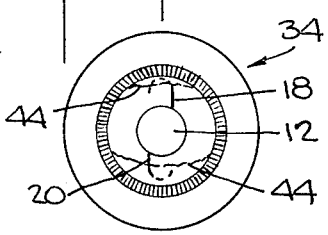
FIG. 4 is a simplified front view of the insert in an eye, looking posteriorly of the iris; and, FIGS. 5 and 6 are simplified plan views of other embodiments of the invention.

The lens body 12 has an optical axis 38, which for the sake of simplicity is presumed to be the geometric center of the lens body. It will also be presumed that the eye has an optical axis 40 passing through the center of the pupil located between the iris 42. The eyeball 34 includes an anterior capsule wall 44 that has been partially removed with the cataract as shown in FIGS. 2 and 4, and a posterior capsule wall 46. It should be noted that after a cataract removal the upper portion of the eye usually has a lesser amount of anterior capsule wall 44 than does the lower portion.

A ciliary sulcus portion 48 of the eye is defined between the iris 42 and the anterior capsule wall 44. The ciliary sulcus 48 extends circumferentially at upper and lower portions of the eye when viewed in cross-section.

Figure 3:
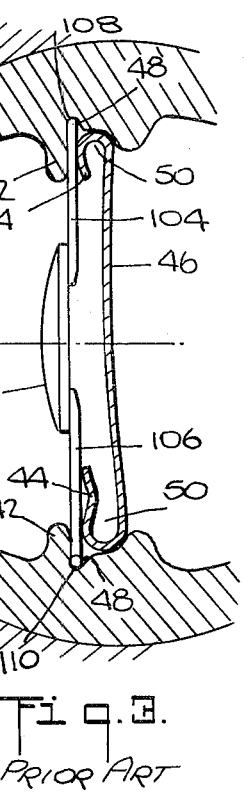
FIG. 3 is representative of the prior art.

A circumferential cul-de-sac portion 50 of the eye is defined between the anterior capsule wall 40 and the posterior capsule wall 46, at upper and lower portions of the eye when viewed in cross-section as shown in FIGS. 2 and 3. The ciliary sulcus 48 and the circumferential cul-de-sac portion 50 are thus interior peripheral surfaces of the eye 34. The interior surface of the ciliary sulcus 48 is approximately 1 to 2 millimeters further away from the optical axis of the eye than the interior peripheral surface of the circumferential cul-de-sac portion 50.

In the embodiment of the intraocular insert shown in FIG. 1, the seating portions 28 and 32 of the position fixation members 18 and 20 are substantially equidistant from the optical axis 38 of the lens body 12. Furthermore, the radial distance of the seating portions 28 and 32 from the optical axis of the lens body 12 is normally greater than the distance between the optical axis of the eye and the interior peripheral surface of the ciliary sulcus 48. However, the cross-section of the position fixation member 20 is less than that of the position fixation member 18 by a predetermined amount so as to enable the seating portion 32 to deflect 1 to 2 millimeters more than the seating portion 28 under a predetermined given force condition.

When the intraocular insert 10 is inserted into the eye, the seating portions 28 and 32 are deflected toward the optical axis of the eye but respectively resiliently bear against the ciliary sulcus 48 and the circumferential cul-de-sac 50. The predetermined force condition previously referred to is thus the force imposed by the ciliary sulcus 48 and the circumferential cul-de-sac 50 on the respective seating portions 28 and 32. Since the seating portion 32 deflects 1 to 2 millimeters more than the seating portion 28, the seating portion 32 can be disposed in the circumferential cul-de-sac 50 whereas the seating portion 28 can be disposed in the ciliary sulcus 48. As the seating portions 28 and 32 are generally coplanar, in a plane which is parallel to the posterior surface 16 of the lens body 12, the lens body 12 is inclined approximately 10° with respect to the vertical, which is within acceptable limits.

Preferably the position fixation members 18 and 20 are formed of the same material. However, this invention also contemplates the use of different materials for the position fixation members, wherein one material is less stiff than the other, the respective stiffnesses being predetermined to ensure that the seating portion 32 deflects 1 to 2 millimeters more toward the optical axis of the eye than the seating portion 28 under force conditions such as are present in the eye when the intraocular insert 10 is positioned as indicated in FIG. 2.

The dimensions of the various components of the intraocular lens 10 are similar to those of the model PC-10, posterior chamber, two loop intraocular lens made by Heyer-Schulte, previously referred to, except for the structural modifications that can be made by persons skilled in the art to accomplish the difference in deflection magnitudes of the respective seating portions 28 and 32 for the given force conditions imposed by the eye on the seating portions.

In another embodiment of the invention, which is also illustrated by the intraocular lens shown in FIG. 2, the seating portion 32 of the position fixation member 20 is formed 1 to 2 millimeters closer to the optical axis of the lens body 12 than the seating portion 28 of the position fixation member 18. The position fixation members 18 and 20 are otherwise formed of the same material and have identical cross-sectional dimensions.

Upon insertion of the intraocular lens in the eye, the position fixation members 18 and 20 are seated as shown in FIG. 2. Since the seating portion 32 of the position fixation member 20 is closer to the optical axis of the lens body than the seating portion 28 of the position fixation member 18, the seating portion 32 can be accommodated in the circumferential cul-de-sac portion 50 whereas the seating portion 28 can be accommodated in the ciliary sulcus 48. The seating portions 28 and 32 deflect equivalent amounts under a given force condition to permit resilient retention of the position fixation member in their respective locations in the eye. As with the embodiment previously described, the seating portions 28 and 32 are substantially coplanar resulting in a slight inclination of the lens body with respect to the vertical.

Figures 5, 6:
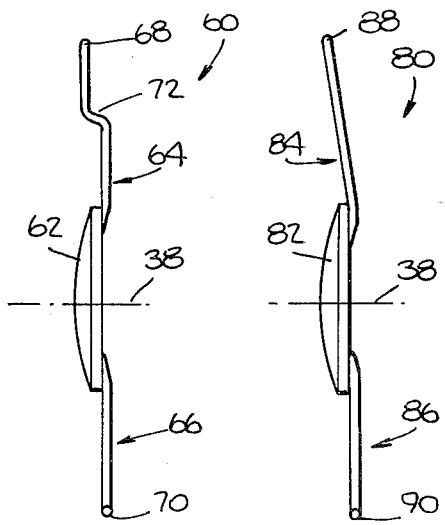

In another embodiment of my invention, an intraocular insert is generally indicated by the reference number 60 in FIG. 5. The intraocular insert 60 includes a lens body 62 corresponding to the lens body 12, and position fixation members 64 and 66 corresponding to the position fixation members 18 and 20. The position fixation member 64 includes a seating portion 68 and the position fixation member 66 includes a seating portion 70. The seating portion 70 is approximately 1 to 2 millimeters closer to the optical axis 38 of the lens body 62 than the seating portion 68 of the position fixation member 64. However, the position fixation member 64 includes a stepped portion 72 which provides a forward offset of the seating portion 68 from the seating portion 70 with respect to the optical axis 38 of the lens body 62. The offset 72 is predetermined so as to enable the lens body 62 to remain substantially vertically disposed in the eye when the seating portion 68 is seated in the ciliary sulcus 48 and the seating portion 70 is seated in the circumferential cul-de-sac portion 50 of the eye.

In a further embodiment of my invention as shown in FIG. 6, an intraocular lens is generally indicated by the reference number 80. The intraocular lens 80 includes a lens body 82 having a position fixation member 84 corresponding to the position fixation member 18 and a position fixation member 86 identical to the position fixation member 66. The position fixation member 84 is inclined a predetermined amount from the vertical approximately seven to twelve degrees, such that a seating portion 88 is forwardly disposed from a seating portion 90 on the position fixation member 86 by an amount that is substantially equivalent to the axial distance between the ciliary sulcus 48 and the circumferential cul-de-sac portion 50 of the eye. The seating portion 90 of the position fixation member 86 is 1 to 2 millimeters closer to the optical axis 38 of the lens body 82 than is the seating portion 88 of the position fixation member 84. The position fixation members 84 and 86 have similar cross-sections and their respective seating portions 88 and 90 deflect substantially equal amounts when subjected to a given force. The intraocular insert 80 is inserted in the eye with the seating portion 88 accommodated by the ciliary sulcus 48 and the seating portion 90 accommodated by the circumferential cul-de-sac portion 50 of the eye. Because of the inclination of the position fixation member 84, the lens body 82 has substantially no inclination with respect to the vertical and there is minimal chafing of the iris by the position fixation member 84.

In each of the embodiments of the invention, only one of the position fixation members is seated in the ciliary sulcus 48 of the eye. Therefore, there is less total force on this region than would be felt if both of the position fixation members were resiliently seated in the ciliary sulcus region 48 as shown by the intraocular insert 100 in FIG. 3.

The prior art intraocular insert 100 includes a lens body 102, a position fixation member 104 and a position fixation member 106 having respective seating portions 108 and 110. The seating portions 108 and 110 are normally equidistant from an optical axis 40 of the lens body 102, and their respective position fixation members have identical cross-sections. The seating portions 108 and 110 of the intraocular insert 100 are resiliently located in upper and lower portions of the ciliary succus region 48 of the eye. However it is not feasible to position the seating portion 110 in the circumferential cul-de-sac portion 50 of the eye because of intolerable forces that woule arise due to the increased deflection requirements for accommodation in the circumferential cul-de-sac portion 50.

While the invention has been disclosed with the position fixation member 18 disposed in the upper portion of the ciliary succus 48, it is contemplated that such orientation can be reversed with the position fixation member 18 disposed in the lower portion of the ciliary sulcus. It is also contemplated that with respect to the embodiment 60 the position fixation member 64 can be free of any step and that the position fixation member 66 can have a step that would likewise assure vertical disposition of the lens body 62 with respect to the optical axis 40 of the eye. It is also contemplated with respect to the embodiment 80 of FIG. 6 that the position fixation member 86 be inclined and that the position fixation member 84 be uninclined to assure vertical disposition of the lens body 82 with respect to the optical axis 40 of the eye.

As will be apparent to those skilled in the art, the position fixation member which is disposed in the ciliary sulcus at the upper portion of the eye can also be disposed in the ciliary sulcus at the lower portion of the eye and the position fixation member which is seated in the circumferential cul-de-sac portion 50 at the lower portion of the eye can be seated in the circumferential cul-de-sac portion 50 at the upper portion of the eye. It is contemplated that the seating portion of one fixation member can have a smaller radius of curvature than that of the other position fixation member to permit viewing behind or positioning thru an iridectomy the position fixation member having the smaller radius of curvature.

Some advantages of the present invention evident from the foregoing description include an intraocular insert which can be resiliently retained in the eye without exerting undesirable force on the ciliary sulcus of the eye, and an intraocular insert that can be relatively easily adjusted in the eye because only one of the position fixation members is seated in the ciliary sulcus portion of the eye.

In view of the above, it will be seen that the several objects of the invention are achieved and other advantageous results attained.

As various changes can be made in the above construction without departing from the scope of the invention, it is intended that all matter contained in the above description or shown in the accompanying drawing should be interpreted as illustrative and not in a limiting sense.

What is claimed is:

1. An intraocular insert suitable for use as an artificial lens in the interior of a human eye, said eye interior having upper and lower portions and including a pupil, an iris and an anterior capsule wall with a ciliary sulcus defined between said iris and said anterior capsule wall, said ciliary sulcus comprising a first interior peripheral surface extending circumferentially at said upper and lower portions of the eye when viewed in cross-section, said eye interior further including a posterior capsule wall and a second interior peripheral surface defined between said anterior capsule wall and said posterior capsule wall, said second interior peripheral surface extending circumferentially at said upper and lower portions of the eye when viewed in cross-section, said eye further including an optical axis passing through the center of said pupil, the distance between said first interior peripheral surface and the optical axis of said eye being greater than the distance between said second interior peripheral surface and the optical axis of said eye, said insert comprising a medial light focusing lens body having an optical axis and first and second opposite peripheral portions, first position fixation means joined to said first peripheral portion and having a first seating portion extending generally radially beyond said first peripheral portion, said first seating portion being engageable with one of said interior peripheral surfaces, second position fixation means being joined to said second peripheral portion of said lens body and having a second seating portion extending generally radially beyond said second peripheral portion, said second seating portion being engageable with the other said interior peripheral surface to substantially align the optical axis of said lens body with the optical axis of said eye, said position fixation means including means for permitting one of said seating portions to be resiliently seated at the first interior peripheral surface of the eye and for permitting the other of said seating portions to be resiliently seated at the second interior peripheral surface of the eye.

2. An intraocular insert as claimed in claim 1 wherein the seating portion of said one position fixation means has a radial extent from the optical axis of said lens body greater by a first predetermined amount than the radial extent of said first interior peripheral surface from the optical axis of said eye to permit resilient seating of said one position fixation means, and the seating portion of the other said position fixation means has a radial extent from the optical axis of said lens body greater by a second predetermined amount than the radial extent of said second interior peripheral surface from the optical axis of said eye, to permit resilient seating of said other position fixation means.

3. An intraocular insert as claimed in claim 2 wherein the radial extent of said one and said other seating portions from the optical axis of said lens body are substantially equivalent and said other position fixation means includes means for permitting a greater magnitude of deflection of its corresponding seating portion than the magnitude of deflection of the seating portion of said one position fixation means in response to a given force on said respective seating portions.

4. An intraocular insert as claimed in claim 3 wherein said other position fixation means is formed of a less stiff material than said one position fixation means, as the means for permitting greater deflection of said other position fixation means.

5. An intraocular insert as claimed in claim 3 wherein said other position fixation means is of the same material as said one position fixation means but is of lesser cross-section than the first position fixation means, as the means for permitting greater deflection.

6. An intraocular insert as claimed in claim 2 wherein the radial extent of said one seating portion from the optical axis of said lens body is greater than the radial extent of said other seating portion from the optical axis of said lens body.

7. An intraocular insert as claimed in claim 6 wherein said one and said other seating portions are substantially coplanar.

8. An intraocular insert as claimed in claim 6 wherein one of said position fixation means is inclined with respect to a plane generally parallel to said lens body and containing the other said position fixation means, to offset the seating portions of said first and said second position fixation means with respect to each other.

9. An intraocular insert as claimed in claim 8 wherein said second position fixation means is inclined with respect to said plane containing said first position fixation means such that the seating portion of said second position fixation means is offset forwardly of the seating portion of said first position fixation means.

10. An intraocular insert as claimed in claim 9 wherein the offset angle is approximately seven to twelve degrees.

11. An intraocular insert as claimed in claim 6 wherein one of said position fixation means includes a leg portion having a step formed thereon to offset the seating portions of said first and said second position fixation means with respect to each other.

12. An intraocular insert as claimed in claim 11 wherein said second position fixation means has said stepped leg portion such that the seating portions of said second position fixation means is offset forwardly of the seating portion of said first position fixation means.

13. An intraocular insert as claimed in claim 6 wherein said position fixation means are formed of a resilient spring-like plastic such as polypropylene.

14. An intraocular insert as claimed in claim 1 wherein one of said position fixation means comprises a first J-shaped position fixation member having a first leg portion affixed to said one peripheral section of said lens body, the curved portion of said first J being at the free end of said first position fixation member to define the seating portion of said first position fixation member.

15. An intraocular insert as claimed in claim 14 wherein the other of said position fixation means comprises a second J-shaped position fixation member, having a second leg portion affixed to the other peripheral section of said lens body, the curved portion of said second J being at the free end of said second position fixation member to define the seating portion of said second position fixation member.

16. An intraocular insert as claimed in claim 15 wherein the seating portion of said one position fixation member has a radial extent from the optical axis of said lens body greater by a first predetermined amount than the radial extent of said first interior peripheral surface from the optical axis of said eye to permit resilient seating of said one position fixation member, and the seating portion of the other said position fixation member has a radial extent from the optical axis of said lens body greater by a second predetermined amount than the radial extent of said second interior peripheral surface from the optical axis of said eye to permit resilient seating of said other position fixation member.

17. An intraocular insert as claimed in claim 14 wherein the radial extents of said one and said other seating portions from the optical axis of said lens body are substantially equivalent and said other position fixation member includes means for permitting a greater magnitude of deflection of its corresponding seating portion than the magnitude of deflection of the seating portion of said one position fixation member in response to a given force on said respective seating portions.

18. An intraocular insert as claimed in claim 17 wherein said other position fixation member is formed of a less stiff material than said one position fixation member, as the means for permitting greater deflection of said other position fixation member.

19. An intraocular insert as claimed in claim 17 wherein said other position fixation member is formed of the same material as said one position fixation member but is of lesser cross-section than the first position fixation member, as the means for permitting greater deflection.

20. An intraocular insert as claimed in claim 15 wherein the radial extent of said one seating portion from the optical axis of said lens body is greater than the radial extent of said other seating portion from the optical axis of said lens body.

21. An intraocular insert as claimed in claim 20 wherein said one and said other seating portions are substantially coplanar.

22. An intraocular insert as claimed in claim 20 wherein one of said position fixation members is inclined with respect to a plane generally parallel to said lens body and containing the other said position fixation member, to offset the seating portions of said first and said second position fixation members with respect to each other.

23. An intraocular insert as claimed in claim 20 wherein said second position fixation member is inclined with respect to said plane containing said first position fixation member such that the seating portion of said second position fixation member is offset forwardly of the seating portion of said first position fixation member.

24. An intraocular insert as claimed in claim 23 wherein the offset angle is approximately seven to twelve degrees.

25. An intraocular insert as claimed in claim 20 wherein one of said position fixation members includes a leg portion having a step formed thereon to offset the seating portions of said first and said second position fixation members with respect to each other.

26. An intraocular insert as claimed in claim 25 wherein said second position fixation member has said stepped leg portion such that the seating portion of said second position fixation member is offset forwardly of the seating portion of said first position fixation member.

27. An intraocular insert as claimed in claim 15 wherein the position fixation members are formed of a resilient spring-like plastic such as polypropylene.

* * * * *